(12) United States Patent
Alam et al.

(10) Patent No.: US 12,325,876 B2
(45) Date of Patent: Jun. 10, 2025

(54) ELECTROSTATIC CONTROL OF IONIC ENVIRONMENT IN A DROPLET BASED PLATFORM FOR BIOLOGICAL APPLICATIONS

(71) Applicant: Purdue Research Foundation, West Lafayette, IN (US)

(72) Inventors: Muhammad Ashraful Alam, West Lafayette, IN (US); Piyush Dak, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 739 days.

(21) Appl. No.: 16/560,960

(22) Filed: Sep. 4, 2019

(65) Prior Publication Data
US 2020/0248230 A1 Aug. 6, 2020

Related U.S. Application Data

(63) Continuation of application No. 15/054,176, filed on Feb. 26, 2016, now abandoned.

(60) Provisional application No. 62/121,207, filed on Feb. 26, 2015.

(51) Int. Cl.
*C12Q 1/686* (2018.01)
*C12Q 1/6806* (2018.01)

(52) U.S. Cl.
CPC ........... *C12Q 1/686* (2013.01); *C12Q 1/6806* (2013.01)

(58) Field of Classification Search
CPC ........ C12Q 2563/116; C12Q 2565/607; C12Q 1/686; C12Q 1/6806; C12Q 2563/159
See application file for complete search history.

(56) References Cited

U.S. PATENT DOCUMENTS

| | | | |
|---|---|---|---|
| 2012/0021918 A1* | 1/2012 | Bashir | B82Y 35/00 506/2 |
| 2012/0176379 A1* | 7/2012 | Farrer | G06T 17/205 345/420 |
| 2017/0176379 A1* | 6/2017 | Bashir | G01N 33/5438 |

OTHER PUBLICATIONS

Dorvel et al., "Silicon Nanowires with High-k Hafnium Oxide Dielectrics for Sensitive Detection of Small Nucleic Acid Oligomers," ACS Nano, June, vol. 6, No. 7, pp. 6150-6164. (Year: 2012).*
Wang et al., "Dendritic copper-cobalt nanostructures/reduced graphene oxide-chitosan modified glassy carbon electrode for glucose sensing," Sensors and Actuators B, January, vol. 195, pp. 1-7. (Year: 2014).*

* cited by examiner

*Primary Examiner* — Young J Kim
(74) *Attorney, Agent, or Firm* — Edmonds & Cmaidalka, P.C.

(57) ABSTRACT

A process and device for electrostatically controlling an ionic environment in a droplet, such as in a droplet-based platform including polymerase-chain reaction (PCR) applications. The process includes providing a chip that comprises at least a pair of electrodes, placing a salt-containing droplet on the chip, and then applying a bias across the electrodes to accumulate ions near surfaces of the electrodes, thereby depleting a bulk salt concentration in regions of the droplet away from the electrodes.

14 Claims, 4 Drawing Sheets

ELECTROSTATIC CONTROL OF IONIC ENVIRONMENT IN A DROPLET BASED PLATFORM FOR BIOLOGICAL APPLICATIONS

CROSS REFERENCE TO RELATED APPLICATIONS

The present patent application is related to and is a continuation of U.S. patent application Ser. No. 15/054,176, filed Feb. 26, 2016, which claims the priority benefit of U.S. Provisional Patent Application Ser. No. 62/121,207, filed Feb. 26, 2015. The contents of all of the above applications are hereby incorporated by reference in their entirety into the present disclosure.

STATEMENT REGARDING FEDERALLY FUNDED RESEARCH

This invention was made with government support under Contract No. EEC-1227020 awarded by the National Science Foundation. The Government has certain rights in the invention.

TECHNICAL FIELD

The present application relates to biological sensing systems and, more specifically, to a biological sensing system that uses electrostatic control of an ionic environment in a droplet based platform.

BACKGROUND

Salt based electrolytes play a fundamentally important role in many chemical/biochemical processes. For example, sodium is found in extracellular fluid and controls blood pressure. Similarly, magnesium ions are typically used for optimization of polymerase chain reaction (PCR), which is important for genome sequencing. Further, ions have recently also found broad applications in flexible and transparent electronics. Precise control of electrolyte concentrations at micro scale levels is essential for many lab on chip technologies.

Much of modern molecular biology is founded on PCR technology. For example, PCR based methods are used in DNA fingerprinting, cloning, phylogenetics, mutagenesis, analysis of gene expression, and numerous other biological studies. In traditional PCR, double stranded DNA is unfolded (melted) at an elevated temperature, then annealed at a lower temperature with short complimentary "primer" DNA, and then copied by a polymerase enzyme starting at the primer at a slightly higher temperature than annealing temperature, but less than the denaturation temperature. The cycle is repeated to generate a suitable amount of DNA for further use. PCR is typically carried out by thermal cycling in sealed tubes, sometimes within water droplets enclosed in oil to combat evaporation.

SUMMARY

According to one aspect, a process for electrostatically controlling an ionic environment in a droplet is provided, comprising providing a chip that comprises at least a pair of electrodes, placing a salt-containing droplet on the chip so that the droplet contacts the pair of electrodes, and then applying a bias across the pair of electrodes to accumulate ions near surfaces of the electrodes, thereby reducing the bulk salt concentration in regions of the droplet away from the electrodes. The droplet may contain DNA wherein the step of applying the bias causes denaturation of the DNA by modification of the melting temperature thereof. The reduction of the bulk salt concentration may reduce the melting temperature of the DNA. The surface of the electrodes is formed to have a dendritic surface morphology.

According to another aspect, a device for controlling an ionic environment in a droplet is provided, comprising a dielectric substrate, a biological sensor mounted to the substrate, and at least a pair of electrodes mounted to the substrate and electrically isolated from each other and from the sensor. The electrodes have a dentritic surface morphology and the biological sensor is disposed between the pair of electrodes. An electronic controller having a computer processor and a memory may be operatively connected to the voltage source and the biological sensor, the electronic controller configured to control the applied voltage and monitor a signal output from the biological sensor.

According to another aspect, a process for performing a polymerase-chain reaction is provided, comprising providing a chip that comprises at least a pair of electrodes, placing a droplet comprising DNA, DNA primer, and polymerase on the chip so that the droplet contacts the pair of electrodes, applying a bias across the pair of electrodes to accumulate ions near surfaces of the electrodes, thereby reducing the bulk salt concentration in regions of the droplet away from the electrodes and denaturing the DNA in the droplet, controlling the temperature of the droplet to achieve annealing of the denatured DNA to the primer, and controlling the temperature of the droplet to achieve extension of the DNA using the polymerase. The droplet may further comprise a reaction buffer solution and deoxynucleoside triphosphates. The DNA primer may further comprise forward and reverse primers. The polymerase may comprise DNA polymerase.

BRIEF DESCRIPTION OF THE DRAWINGS

In the following description and drawings, identical reference numerals have been used, where possible, to designate identical features that are common to the drawings.

The attached drawings are for purposes of illustration and are not necessarily to scale.

DETAILED DESCRIPTION

Various aspects relate to electrostatic control of an ionic environment in a droplet based platform for biological applications. The terms "I," "we," "our" and the like throughout this description do not refer to any specific individual or group of individuals.

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 1:
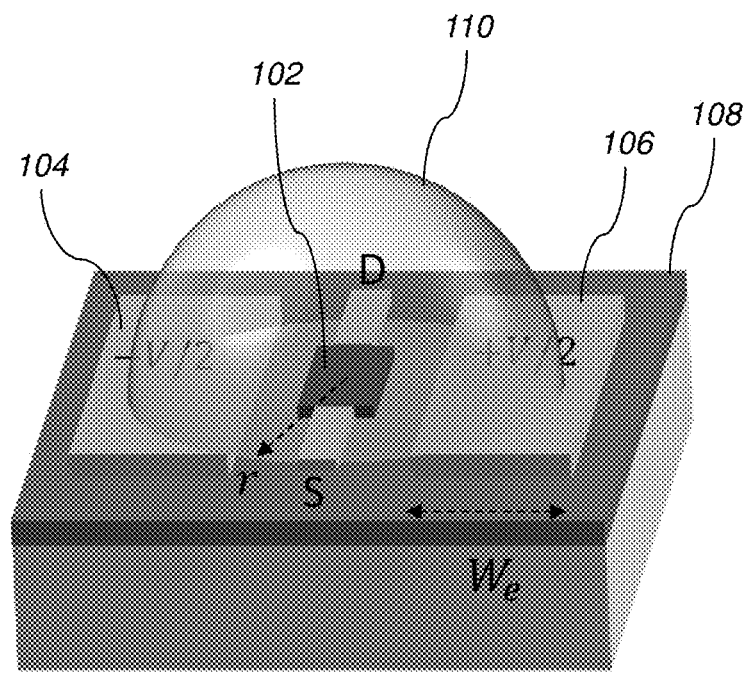
FIG. 1 is a diagram showing a system for desalting a micro-droplet according to various aspects.

The present invention provides a technique and device adapted to electrostatically control an ionic environment in a droplet, for example, in a droplet-based sensing system. FIG. 1 shows a diagram of a droplet-based sensing system 100 according to one embodiment. As shown, the system 100 comprises a sensor 102 and electrodes 104 and 106 mounted on a substrate 108. The electrodes 104 and 106 may comprise any electrically conductive material, including, but not limited to, metals such as gold, silver, aluminum, and the like. The substrate is preferably a dielectric material to electrically isolate the electrodes 104 and 106 from each other and from the sensor 102. The electrodes 104 and 106 may also be physically separated from the sensor 102 and from one another to define a region around the sensor 102 which is distant from the electrodes 104 and 106.

A fluid micro-droplet 110 (shown with radius r) is placed on the system 100 and contacts the electrodes 104 and 106, and the sensor 102. The micro-droplet 110 has a volume preferably in the range of ten nanoliters or less. In certain embodiments, the droplet 110 has a volume of less than one nanoliter. The droplet solution comprises a salt, and a bias is applied across the electrodes 104 and 106 to accumulate ions near the electrode surfaces, thereby depleting the bulk salt concentration in regions of the micro-droplet 110 away from the electrodes. The droplet 110 may comprise various shapes, including, but not limited to, a hemisphere, a half-ellipsoid, an elongated half-spherical shape, or any shape resulting from placing a liquid droplet onto a surface or patterned channel or repository.

Bulk desalting of a droplet as described above may potentially enable a broad range of applications, nonlimiting examples of which involve droplet-based platforms. Particular examples include the modulation of pH profile for isoelectric protein separation, electrostatic denaturation of DNA by modification of the melting temperature of DNA, and improving the detection limits of biosensors used for early-disease detection.

Figure 2:
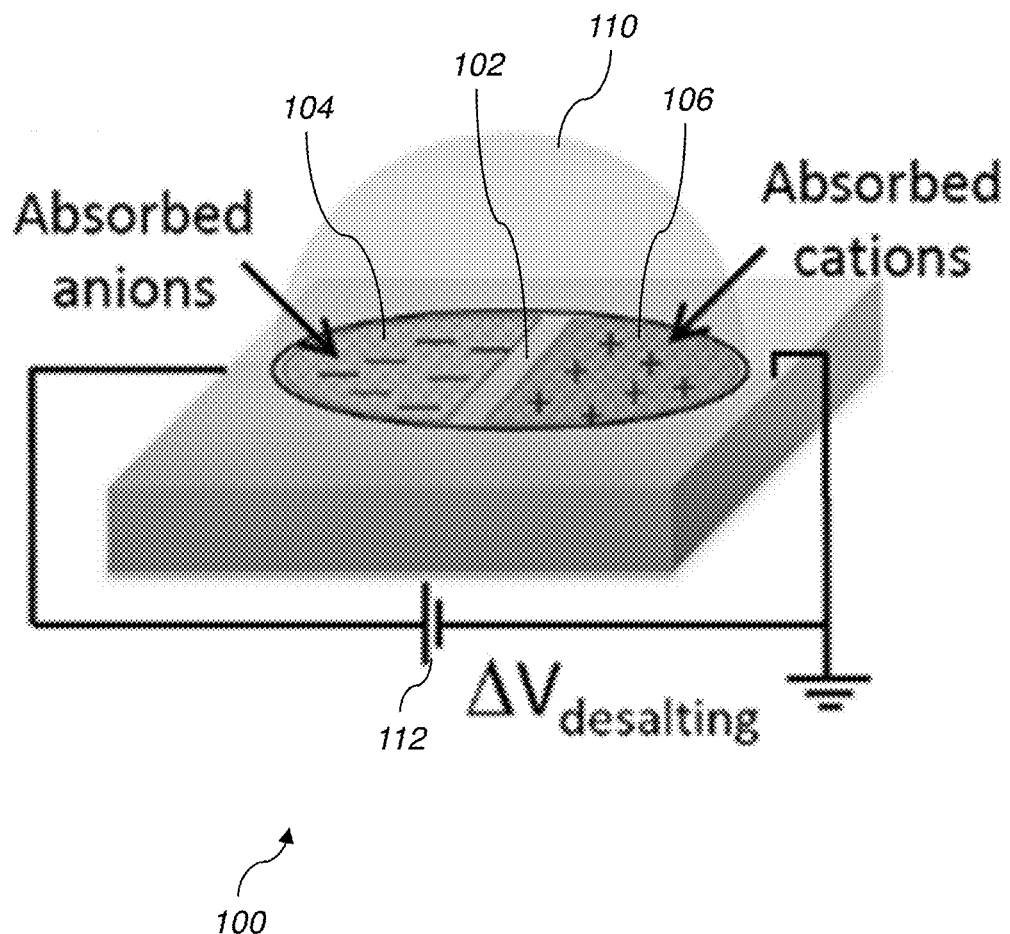
FIG. 2 is a diagram illustrating operation of the device of FIG. 1 according to various aspects.

In a particular but nonlimiting example, a process of the type described above enables PCR to be accomplished in microdroplets (for example, of droplets having a volume less than 10 nanoliters, such as micro-droplet 110) at lower temperatures than is possible in prior art methods. In one embodiment of the present disclosure, PCR is accomplished by providing a buffer solution which contains positive ions that stabilize negatively charged DNA within a droplet, such as the micro-droplet 110. The droplet is placed on the system 100 so as to contact the two electrodes 104 and 106 on the chip, and a bias is applied (e.g., using a voltage source 112) across the electrodes 104 and 106 to accumulate the positive ions near the surface of the negative electrode, and negative ions near the surface of the positive electrode as shown in FIG. 2. This depletes the bulk of the positive ions in the volume of the droplet away from the electrodes, resulting in a deionized region near the sensor 102. The DNA in the droplet 110 is therefore destabilized because the effective positive ion concentration is reduced, with the result that the melting temperature of the DNA is reduced, potentially to a temperature near or below room temperature. Consequently, melting of the DNA does not necessarily require the application of additional heat (as is required in prior art methods), and the process facilitates a lower-temperature, voltage-controlled PCR reaction (due to a decrease in ionic concentration). Following melting of the DNA, further steps can be performed as necessary for the particular application to complete the PCR analysis.

Also, while using DNA polymerase during PCR, magnesium ions are typically incorporated into PCR solutions. However, PCR does not result if the magnesium ion concentration is very low, but an excessively high magnesium ion concentration can lead to a variety of unwanted products. In one embodiment of a method using the system 100, the applied bias is applied and controlled to modulate the magnesium ion concentration in the droplet 110 so as to optimize PCR performance.

In certain embodiments, an electronic controller, having a computer processor and memory, may be operatively connected to the electrodes 104 and 106 to automatically control the bias voltage applied to the droplet 110 as described in the above process. The computer processor and memory may contain computer readable instructions for carrying out a desalting process on the droplet and optimizing the required voltage bias being applied by the voltage source 112.

Another notable aspect of the disclosed system 100 relates to reuse of the system 100 components. In prior art methods, in order to reuse a DNA sensor that relies on binding between receptor (e.g., single strand DNA oligonucleotides coated on the surface of the sensor) and analyte (e.g., complimentary DNA strands present in a solution), heat is applied to remove the analyte from the receptors on the sensor surface. However, using the presently disclosed system 100, analytes may be removed by decreasing the ionic concentration near the sensor 102 by adjusting the bias applied to the electrodes 104 and 106, after which the sensor (which is still coated with the receptor) can be reused with a different analyte (or same analyte with unknown concentration). Such a capability is referred to herein as modulation of an analyte and receptor interaction, and promotes the reusability of the device.

Figure 3:
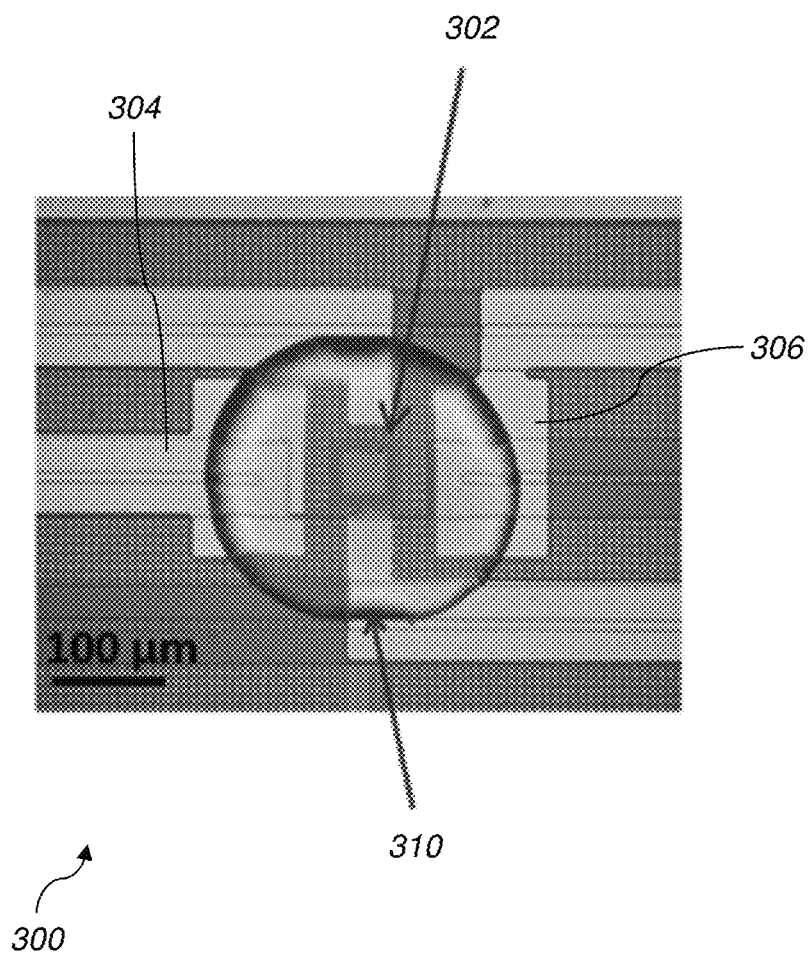
FIG. 3 is image of a micro-patterned system similar to the system of FIG. 1.

In certain embodiments, the system 100 may be fabricated as micro-patterned electrodes (each having a dimension in the range of 100 μm×100 μm) using evaporation and lift-off patterning of 1000 Å thick Ti/Pt films. FIG. 3 shows a micrograph image showing a system 300, similar to system 100, having two pairs of on-chip desalting electrodes 304 and 306 patterned around a transducer 302 and encapsulated within an applied droplet 310 according to a further embodiment.

Figure 4:
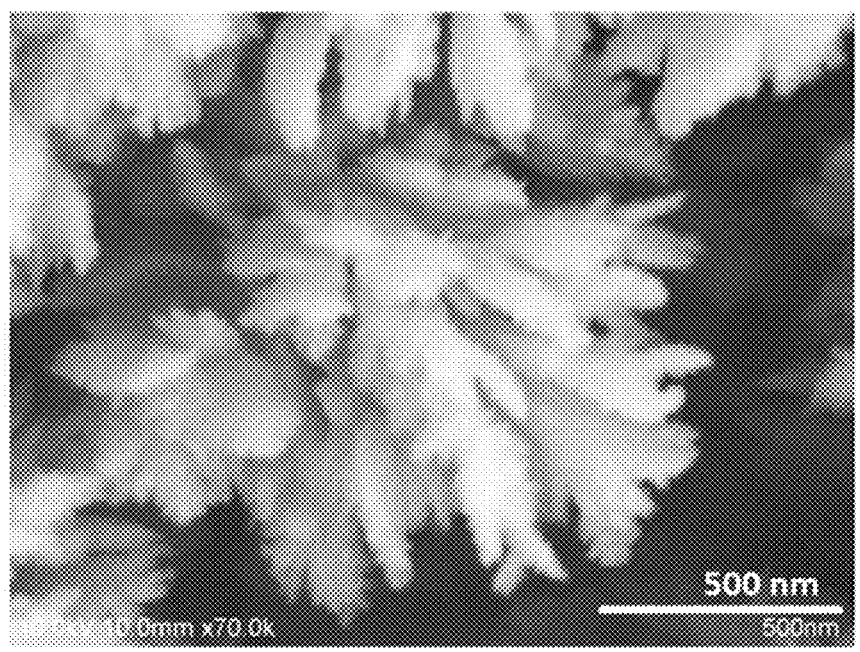
FIG. 4 shows an SEM image of an electrode having increased surface area according to various aspects.

In certain applications, the electrodes 104 and 106 may be formed to have increased surface area, such as by forming a non-planar material on the substrate. In one embodiment, the electrodes are form by galvanostatically depositing platinum-black (Pt-black) on a seed layer Ti/Pt. This results in electrodes having a fractal, branched or dendritic surface morphology. In certain embodiments, the electrodes having such a fractal, branched, or dendritic surface morphology may have a critical dimension in the resulting nano structure on the order of less than 50 nm. This increases the ratio of electrode surface area in contact with the applied micro-droplet 110 to volume of the micro-droplet 110, and allows desalting of higher concentration salt solutions. FIG. 4 show a scanning electron microscope (SEM) image of the surface of a sample Pt-black electrode 404 (similar to electrodes 104 and 106) formed using the above process.

Steps of various methods described herein can be performed in any order except when otherwise specified, or when data from an earlier step is used in a later step. Exemplary method(s) described herein are not limited to being carried out by components particularly identified in discussions of those methods.

According to various aspects, technical effects can include the capability for reducing temperatures required to melt DNA, modulating magnesium ion concentrations for PCR optimization, modulating interactions between analyte molecules and receptors for sensor reusability (when analyte and receptor are DNA strands), and generally improving biochemical sensing technologies.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media may embody computer-readable instructions, data structures, program modules, or other data in a modulated data signal, such as a carrier wave or other transmission mechanism. As defined herein, "computer storage media" do not include communication media. That is, computer storage media do not include communications media consisting solely of a modulated data signal, a carrier wave, or a propagated signal, per se.

The invention is inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless otherwise explicitly noted. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected within the spirit and scope of the invention.

The invention claimed is:

1. A device for controlling an ionic environment in a droplet, comprising:
   a dielectric substrate;
   a biological sensor mounted to the substrate;
   and at least a pair of electrodes mounted to the substrate and electrically isolated from each other and from the sensor, the electrodes having a dentritic surface morphology;
   wherein the biological sensor is disposed between the pair of electrodes.

2. The device of claim 1, wherein the dentritic surface morphology is formed from Pt-black.

3. The device of claim 2, wherein each electrode is independently controlled to apply a different voltage.

4. The device of claim 1, further comprising a voltage source connected across the pair of electrodes, the voltage source configured to apply a voltage bias across the pair of electrodes to accumulate ions near surfaces of the electrodes when a droplet is placed on the sensor and the electrodes, thereby reducing the bulk salt concentration in regions of the droplet away from the electrodes.

5. The device of claim 4, further comprising an electronic controller having a computer processor and a memory, the electronic controller operatively connected to the voltage source and the biological sensor, the electronic controller configured to control the applied voltage and monitor a signal output from the biological sensor.

6. The device of claim 1, wherein the biological sensor is a DNA sensor.

7. The device of claim 6, wherein the DNA sensor is coated with a receptor DNA material.

8. A device for controlling an ionic environment in a droplet, comprising:
   a dielectric substrate;
   a biological sensor mounted to the substrate; and
   at least two electrodes mounted to the substrate, each electrode being electrically isolated from the other and electrically isolated from the sensor, and wherein:
   at least one electrode has a dendritic surface morphology, and
   the biological sensor is disposed between the electrodes.

9. The device of claim 8, wherein the dendritic surface morphology is formed from Pt-black.

10. The device of claim 9, further comprising independent voltage sources connected to each electrode, each voltage source configured to apply a voltage the corresponding electrode to accumulate, depending on the voltage polarity, positive or negative ions near surfaces of the electrodes when a droplet is placed on the sensor and the electrodes, thereby reducing the bulk salt concentration in regions of the droplet away from the electrodes.

11. The device of claim 10, further comprising an electronic controller having a computer processor and a memory, the electronic controller operatively connected to the voltage source and the biological sensor, the electronic controller configured to control the applied voltage and monitor a signal output from the biological sensor.

12. The device of claim 8, wherein the biological sensor is a DNA sensor.

13. The device of claim 12, wherein the DNA sensor is coated with a receptor DNA material.

14. The device of claim 8, wherein each electrode is independently controlled to apply voltage.

* * * * *